United States Patent [19]

Enders et al.

[11] 4,060,628

[45] Nov. 29, 1977

[54] 2-(ALKYLHALOPHENYLIMINO)DITHIO-LANES AND ECTOPARASITICIDAL COMPOSITION AND METHOD

[75] Inventors: Edgar Enders, Cologne; Wilhelm Stendel, Wuppertal, both of Germany

[73] Assignee: Bayer Aktiengesellschaft, Germany

[21] Appl. No.: 714,401

[22] Filed: Aug. 16, 1976

[30] Foreign Application Priority Data

Aug. 22, 1975  Germany .............................. 2537379

[51] Int. Cl.$^2$ ...................... A01N 9/12; C07D 339/06
[52] U.S. Cl. .................................. 424/277; 260/327 M
[58] Field of Search .................... 260/327 M; 424/277

[56] References Cited

U.S. PATENT DOCUMENTS

| 3,442,907 | 5/1969 | Donche et al. ...................... 260/327 |
| 3,484,455 | 12/1969 | Addor .................................. 260/327 |
| 3,489,771 | 1/1970 | Donche et al. ...................... 260/327 |
| 3,954,801 | 5/1976 | Addor et al. ...................... 260/327 M |

*Primary Examiner*—Richard L. Raymond
*Attorney, Agent, or Firm*—Jacobs & Jacobs

[57] ABSTRACT

2-(Alkylhalophenylimino)-1,3-dithiolanes are ectoparasiticidal agents. The compounds, of which 2-(2-methyl-4-chlorophenylimino)-1,3-dithiolane is a typical example, are obtained by condensation of a salt of the corresponding N-phenyldithiocarbamic acid and a vic-dihaloalkane.

10 Claims, No Drawings

2-(ALKYLHALOPHENYLIMINO)DITHIOLANES AND ECTOPARASITICIDAL COMPOSITION AND METHOD

The present invention relates to new substituted 2-phenylimino-1,3-dithiolanes and to processes for their preparation and use as ectoparasiticidal agents.

It is known that 2-arylimino-1,3-dithietanes exert action against acarides; see e.g. German Offenlegungsschrift 23 05 517. These compounds are however less active than the substituted 2-phenylimino-1,3-dithiolanes of the present invention.

The present invention provides substituted 2-phenylimino-1,3-dithiolanes of the formula:

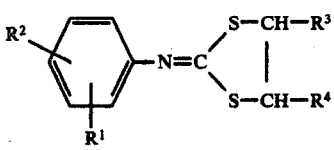

and the physiologically acceptable salts thereof wherein $R^1$ is alkyl of 1 to 6 carbon atoms;
$R^2$ is halo; and
each of $R^3$ and $R^4$ is hydrogen or alkyl of 1 to 6 carbon atoms.

$R^1$, $R^3$ or $R^4$ are straight or branched chained alkyl with 1 to 6, especially 1 to 4, carbon atoms, such as methyl, ethyl, n- and i-propyl, and n-, i- and t-butyl. $R^2$ is halo such as fluoro, chloro, bromo or iodo, especially chlorine and bromine.

The alkyl groups $R^1$, $R^3$ and $R^4$ can be optionally substituted with alkoxy of 1 to 6, especially 1 to 4, carbon atoms, such as, for example, methoxy, ethoxy, n-propoxy and i-propoxy, or alkylthio with 1 to 6, especially 1 to 4, carbon atoms, such as, for example, methylthio, ethylthio, n-propylthio and i-propylthio.

Surprisingly, the compounds of the invention exhibit substantially greater ectoparasiticidal action than the 2-arylimino-1,3-dithietanes known from the state of the art (see German Specification No. 23 05 517). The most active compound disclosed therein, 2-(2-methyl-4-chlorophenyl-imino)-1,3-dithietane, has an ovicidal action on *Boophilus microplus* from a concentration of 500 ppm upwards, while 2-(2-methyl-4-chlorophenyl)-imino-1,3-dithiolane according to the present application is active at a concentration of 250 ppm.

The substituted 2-phenylimino-1,3-dithiolanes are obtained according to a process which comprises condensing a N-phenyldithiocarbamate of the formula:

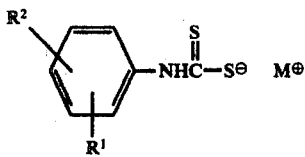

wherein $R^1$ and $R^2$ are as herein defined and M is a cation with a vic-dihaloalkane of the formula:

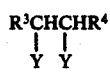

wherein $R^3$ and $R^4$ are as herein defined; and Y is chloro or bromo, and if desired, forming a physiologically acceptable salt thereof.

The resulting compounds can be converted into salts by conventional techniques.

If potassium N-(2-methyl-4-chlorophenyl)-dithiocarbamate and 1,2-dibromoethane are used as starting materials, the course of the reaction can be represented by the following equation:

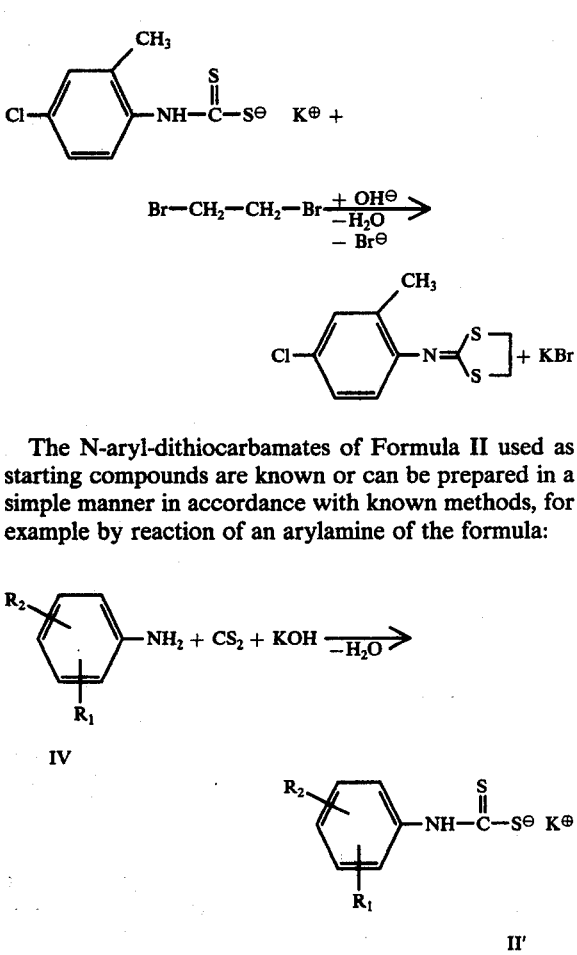

The N-aryl-dithiocarbamates of Formula II used as starting compounds are known or can be prepared in a simple manner in accordance with known methods, for example by reaction of an arylamine of the formula:

$$R_2\text{-}C_6H_3(R_1)\text{-}NH_2 + CS_2 + KOH \xrightarrow{-H_2O}$$

IV $$R_2\text{-}C_6H_3(R_1)\text{-}NH\text{-}C(=S)\text{-}S^\ominus K^\oplus$$

II' wherein $R^1$ and $R^2$ are as herein defined, with carbon disulphide and alkali metal hydroxide, ammonium hydroxide, ammonia or tertiary aliphatic amine in a solvent (see also Houben Weyl, 'Methoden der organischen Chemie', Volume 9, pages 824 to 827).

The following are examples of arylamines of Formula IV: 2-methyl-4-chloro-aniline, 2-methyl-4-bromo-aniline, 2-methyl-4-fluoro-aniline, 2-ethyl-4-chloro-aniline, 2-ethyl-4-bromo-aniline, 2-propyl-4-chloro-aniline, 2-isopropyl-4-chloro-aniline, 2-isopropyl-4-bromo-aniline, 2-methoxymethyl-4-chloro-aniline and 2-methylthiomethyl-4-chloro-aniline.

The following are examples of appropriate salts of N-aryl-dithiocarbamic acids: the sodium, potassium, lithium, ammonium or triethylammonium salts of N-(2-methyl-4-chloro-phenyl)-dithiocarbamic acid; the sodium, potassium or barium salt of N-(2-methyl-4-bromo-phenyl)-dithiocarbamic acid; the ammonium or zinc salt of N-(2-methyl-4-fluoro-phenyl)-dithiocarbamic acid; the sodium or potassium salt of N-(2-ethyl-4-chloro-phenyl)-dithiocarbamic acid; the potassium or ammonium salt of N-(2-ethyl-4-bromo-phenyl)-dithiocarbamic acid, the sodium or potassium salt of N-(2-isopropyl-4-chloro-phenyl)-dithiocarbamic acid; the sodium or potassium salt of N-(2-isopropyl-4-bromo-phenyl)-dithiocarbamic acid.

The following are examples of dihalogenoalkanes of Formula III: 1,2-dibromoethane, 1,2-dichloroethane, 1,2-dibromopropane, 1,2-dichloropropane, 1,2-dibromobutane, 1,2-dibromopentane, 2,3-dichlorobutane and 2,3-dibromopentane.

The reaction of the substituted N-phenyl-dithiocarbamates of Formula II with the dihalogenoalkanes of Formula III is appropriately carried out in a solvent at temperatures of 0°–100° C, preferably at 10°–60° C, in the presence of acid-binding agents. Suitable solvents which may be mentioned are alcohols and ethers such as methanol, ethanol, isopropanol, glycol monomethyl ether, 1,2-dimethoxyethane, dioxane and tetrahydrofurane; ketones, such as acetone, butanone and methyl isopropyl ketone; carboxylic acid derivatives such as ethyl acetate, acetonitrile, dimethylformamide and dimethylacetamide; aromatics and aliphatics such as benzene, toluene, chlorobenzene, xylene, cyclohexane, benzines and ligroins with boiling ranges between 60° C and 180° C; other polar solvents such as dimethylsulphoxide, N-methylpyrrolidone, tetramethylurea and hexamethylphosphoric acid triamide.

Examples of suitable acid-binding agents for the reaction according to the invention are sodium bicarbonate, disodium phosphate, trisodium phosphate, sodium acetate, sodium carbonate, ammonium carbonate, potassium carbonate, sodium hydroxide, potassium hydroxide, triethylamine and ammonia.

A suitable embodiment of the reaction according to the invention is to follow the preparation of the substituted N-phenyl-dithiocarbamate of Formula II, from the arylamine of Formula IV, carbon disulphide and a base, by the further reaction with the dihalogenoalkane of Formula III, without intermediate isolation of a compound of Formula II. In this case, the acid-binding agent can be introduced at the start or only be added subsequently. In general, molar amounts, or a slight excess, of dihalogenoalkane of Formula III relative to substituted N-phenyl-dithiocarbamate of Formula II, are employed, for example an excess of 5 to 15 mol percent.

The reaction mixtures are suitably worked up by mixing with water to remove the salts, extraction of the reaction product with a water-insoluble solvent, and crystallization or distillation. Because of their basic properties, the substituted 2-phenylimino-1,3-dithiolanes are soluble in aqueous mineral acids, for example dilute hydrochloric acid, sulphuric acid or nitric acid, and can be separated out from such solutions in the form of the bases or also as salts. The compounds can, however, also be dissolved in organic solvents and be converted, by addition of the inorganic or organic acid, into their salts, for example into the hydrobromides, phosphates, formates, oxalates, acetates, succinates, trifluoroacetates, benzenesulphonates, benzoates and naphthalene-1,4-disulphonates.

The following may be mentioned individually as new active compounds: 2-(2-methyl-4-chloro-phenylimino)-1,3-dithiolane, 2-(2-methyl-4-bromo-phenylimino)-1,3-dithiolane, 2-(2-ethyl-4-chloro-phenylimino)-1,3-dithiolane, 2-(2-ethyl-4-bromo-phenylimino)-1,3-dithiolane, 2-(2-propyl-4-chloro-phenylimino)-1,3-dithiolane, 2-(2-isopropyl-4-bromo-phenylimino)-1,3-dithiolane, 2-(2-methyl-4-chloro-phenylimino)-4-methyl-1,3-dithiolane, 2-(2-methyl-4-bromo-phenylimino)-4-methyl-1,3-dithiolane, 2-(2-ethyl-4-bromo-phenylimino)-4-methyl-1,3-dithiolane, 2-(2-methyl-4-chloro-phenylimino)-4,5-dimethyl-1,3-dithiolane, 2-(2-methyl-4-chloro-phenylimino)-4-ethyl-1,3-dithiolane, 2-(2-methyl-4-chloro-phenylimino)-4-propyl-1,3-dithiolane and 2-(2-methylthiomethyl-4-chlorophenylimino)-1,3-dithiolane.

The substituted 2-phenylimino-1,3-dithiolanes of Formula I and their salts exhibit a powerful acaricidal action, especially against acarides which, as animal ectoparasites, attack domesticated animals such as cattle, sheep and rabbits. At the same time, the 2-arylimino-1,3-dithiolanes have only a low toxicity towards warm-blooded animals. They are therefore very suitable for combatting animal ectoparasites from the class of the acarides. In addition, however, they also have an action against other ectoparasites, such as insects.

The following may be mentioned as examples of economically important ectoparasites of this species which play a major role especially in tropical and subtropical countries: the Australian and South American one-host cattle tick Boophilus microplus and the South African cattle tick Boophilus decoloratus, both from the family Ixodidae, African multi-host cattle and sheep ticks, such as for example, Rhipicephalus appendiculatus, Rhipicephalus evertsi, Amblyomma hebraeum, Hyalomma truncatum, as well as the South American multi-host cattle ticks, such as, for example, Amblyomma cajennense and Amblyomma americanum.

In the course of time ticks, in particular, have become resistant against the phosphoric acid esters and carbamates hitherto used as agents for combating them, so that the success in combating them is increasingly becoming questionable in numerous regions. To ensure economical animal husbandry in the regions where infection is prevalent, there is an urgent need for agents by means of which all stages of development, that is to say larvae, nymphae, metanymphae and adults, even of resistant strains, for example of the genus Boophilus, can be combated reliably. For example, in Australia the Mackay strain, the Mt.-Alford strain and the Biarra strain of Boophilus microplus are highly resistant to the phosphoric acid esters used hitherto.

The active compounds according to the invention are equally active both against the normally sensitive strains and against the resistant strains, for example of Boophilus. When applied in the usual manner to the host animal, they both have a direct destructive effect on all forms parasitic on the animal and/or cause their release from the host animal, and have a strong ovicidal effect on the adult forms, so that the reproductive cycle of the ticks both in the parasitic phase on the animal and in the non-parasitic phase is interrupted. The laying of eggs is prevented and development and hatching are inhibited.

The present invention therefore provides ectoparaciticidal compositions containing a compound according to the invention as an active ingredient, in admixture with a solid or liquefied gaseous diluent, or in admixture with a liquid diluent other than a solvent of molecular weight less than 200 (preferably less than 300) except in the presence of a surface active agent.

The invention also includes a method of combating ectoparasites which comprises applying to the ectoparasites, or a habitat thereof, such as the skin, hide or coat of an animal, the compound of the invention either alone or in admixture with a diluent or carrier.

The active compounds according to the present invention can be converted into ectoparasiticidal formulations, such as solutions, emulsions, suspensions, powders, pastes and granulates, in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol, or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By "liquefied gaseous diluents or carriers" are meant liquids which would be gaseous at normal temperatures and pressures, for example aerosol propellants, such as halogenated hydrocarbons, for example "Freon".

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

admixed to the formulations or the ready-to-use solutions.

The aqueous solutions or emulsions of the active compounds according to the invention possess good stability under conditions encountered in practice, so that the ready-to-use forms as employed remain active after standing in a pH range of 7–9 for three months or more.

The following examples illustrates the efficacy of the compounds of the invention: In vivo tick test on Boophilus microplus 3 parts of active compound were mixed with 7 parts of a mixture of equal parts by weight of ethylene glycol monomethyl ether and nonylphenyl polyglycol ether. The emulsion concentrate thus obtained was diluted with water to the particular use concentration desired.

Cattle which had been infected repeatedly (12 infections, at intervals of 2 days) with resistant tick larvae of the species Boophilus microplus, Biarra strain, were sprayed with the active compound preparation thus obtained.

The action of the active compound preparation was assessed by determining the number of adult female ticks which develop on the treated cattle. This number is compared with the number of adult female ticks which develop on untreated cattle. The more active the compound, the fewer female ticks develop after the treatment.

The number of adult females which, on treated and untreated animals, develop in the last three days before the treatment time, is used as a measure of the severity of the infection before the treatment.

| Active compound from Example 1 Concentration in ppm | Number of ticks with fertile eggs | | | | | | | | | Action in % |
|---|---|---|---|---|---|---|---|---|---|---|
| | Days before treatment $-2-\pm 0$ | Days after treatment | | | | | | | | |
| | | +1-3 | 4-6 | 7-9 | 10-12 | 13-15 | 16-18 | 19-21 | +1-21 | |
| 250 | 973 | 12 | 0 | 0 | 11 | 1 | 0 | 0 | 24 | 98.95 |
| 500 | 1,112 | 43 | 0 | 0 | 6 | 0 | 1 | 0 | 50 | 98.76 |
| Untreated control | 1,425 | 1,141 | 1,247 | 771 | 309 | 159 | 155 | 23 | 4,105 | — |

|—Adults—| |—Nymphae—| |—Larvae—|
|—Metanymphae—| |Metalarvae|

Approximate stage of development at the time of treatment

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The formulations in general contain from 0.1 to 95% by weight of active compound, more usually from 0.5 to 90% by weight. The use concentrations are prepared from the formulations (see above) by dilution with water. They can, depending on the use form, be varied within a substantial range and lie between 10 and 50,000 ppm (g/g), preferably between 50 and 500 ppm.

The formulations are applied in the usual manner, for example by spraying or pouring-on or atomising, or as a bath (dip).

Other auxiliaries or active compounds, such as disinfectants or particularly suitable insecticides, can also be The following examples illustrate the preparation of particular compounds of the invention.

EXAMPLE 1

2-(2-Methyl-4-chloro-phenylimino)-1,3-dithiolane 50.0 g of 2-methyl-4-chloroaniline were dissolved in 300 ml of dimethylformamide and 27.0 g of carbon disulphide and 23.0 g of potassium hydroxide powder (about 88% strength) were introduced at 5–10° C, with cooling. The mixture was stirred for a further 2 hours and the solution thus obtained was added slowly, with stirring, to a mixture of 200 ml of dimethylformamide, 68 g of dibromoethane and 31 g of sodium bicarbonate. The mixture was kept at 60° C for a further 3 hours and was concentrated in vacuo to half its volume. 300 ml of benzene were added and the whole was stirred into 2 liters of water. The benzene layer was separated off, washed with water, dried over potassium carbonate and fractionated in vacuo.

Boiling point: 173°–180° C/o.8 mm Hg, yield 57.0 g. Analysis: $C_{10}H_{10}ClNS_2$, molecular weight 243.78 calculated. C 49.27 H 4.13 Cl 14.54 N 5.75 S 26.31, found. C 49.5 H 4.3 Cl 14.5 N 5.9 S 26.1; C 49.5 Cl 14.4 N 5.9 S 25.9.

The NMR spectrum agrees with the assumed structure.

EXAMPLE 2

2-(2-Methyl-4-bromo-phenylimino)-1,3-dithiolane

The procedure of Example 1 was repeated, replacing the 2-methyl-4-chloroaniline with 65.0 g of 2-methyl-4-bromo-aniline. 2-(2-Methyl-4-bromo-phenylimino)-1,3-dithiolane of boiling point: 188°–195° C/0.4 mm Hg was obtained.

EXAMPLE 3

2-(2-Methyl-4-chlorophenylimino)-4-methyl-1,3-dithiolane 40.0 g of the triethylammonium salt of N-(4-chloro-2-methylphenyl)dithiocarbamic acid were introduced, at 10° C, into a suspension of 20 g of sodium bicarbonate in 120 ml of dimethylformamide and 26 g of 1,2-dibromopropane. The mixture was stirred for 1 hour at 20° C and 1 hour at 60° C. It was diluted with 300 ml of methylene chloride and then poured into 1 liter of water and 50 ml of 40% strength sodium hydroxide solution. The methylene chloride layer was then separated off, washed with water, dried over potassium carbonate and fractionated:

boiling point: 200°–205° C/1.0 mm Hg; yield: 22.0 g

The analysis and NMR spectrum agree with the indicated structure.

The triethylammonium salt of N-(4-chloro-2-methylphenyl)-dithiocarbamic acid, used as the starting material, can be prepared in accordance with the following instruction: 233 g of 4-chloro-2-methylaniline are dissolved in 1.0 liter of wash benzine and 122 g of carbon disulphide and 171 g of triethylamine are added dropwise. The mixture is stirred for a further hour at 20° C and the ammonium salt which has precipitated is filtered off, washed with petroleum ether and dried.

Yield 460 g; melting point: 93°–95° C.

What is claimed is:

1. A compound selected from the group consisting of a 2-phenylimino-1,3-dithiolane of the formula:

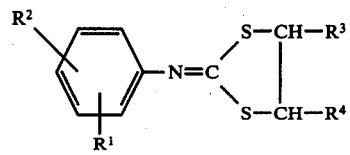

and the physiologically acceptable salts thereof wherein
$R^1$ is alkyl of 1 to 6 carbon atoms;
$R^2$ is halo; and
each of $R^3$ and $R^4$ is hydrogen or alkyl of 1 to 6 carbon atoms.

2. A compound according to claim 1 wherein said 2-phenylimido-1,3-dithiolane is of the formula:

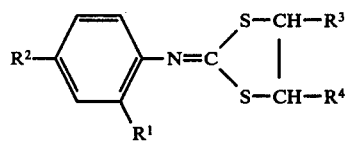

wherein $R^1$, $R^2$, $R^3$ and $R^4$ are as therein defined.

3. A compound according to claim 2 wherein
$R^1$ is alkyl of 1 to 4 carbon atoms;
$R^2$ is chloro or bromo; and
each of $R^3$ and $R^4$ is hydrogen or alkyl of 1 to 4 carbon atoms.

4. A compound according to claim 3 wherein $R^1$ is methyl and each of $R^3$ and $R^4$ is hydrogen or methyl.

5. A compound according to claim 4 wherein each of $R^3$ and $R^4$ is hydrogen.

6. A compound according to claim 1 which is 2-(2-methyl-4-chlorophenylimino)-1,3-dithiolane.

7. The compound according to claim 1 which is 2-(2-methyl-4-bromophenylimino)-1,3-dithiolane.

8. The compound according to claim 1 which is 2-(2-methyl-4-chlorophenylimino)-4-methyl-1,3-dithiolane.

9. An ectoparasiticidal composition comprising an effective amount of a compound according to claim 1 in combination with a solid, liquid or liquefied gaseous diluent.

10. A method of combatting ectoparasites on animals which comprises topically applying an effective amount of a compound according to claim 1.

* * * * *